United States Patent [19]
Gold

[11] 3,941,885
[45] Mar. 2, 1976

[54] COMPOSITIONS USEFUL FOR TREATING PARKINSONISM

[75] Inventor: Elijah H. Gold, West Orange, N.J.

[73] Assignee: Schering Corporation, Kenilworth, N.J.

[22] Filed: Mar. 3, 1975

[21] Appl. No.: 554,807

Related U.S. Application Data

[62] Division of Ser. No. 408,021, Oct. 19, 1973, Pat. No. 3,891,697.

[52] U.S. Cl. .................................. 424/305; 424/317
[51] Int. Cl.[2] .................. A61K 31/19; A61K 31/215
[58] Field of Search ..................... 424/308, 317, 305

*Primary Examiner*—Stanley J. Friedman
*Attorney, Agent, or Firm*—Bruce M. Eisen; Stephen B. Coan

[57] ABSTRACT

Disclosed herein are compounds of the formula:

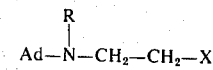

wherein Ad is 1-adamantyl; R is H or $CH_3$; X is COOM or $CH_2$

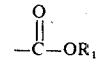

wherein M is H or a pharmaceutically acceptable cation, and $R_1$ is lower n-alkyl; and the pharmaceutically acceptable salts thereof.

Preferred are ethyl-4-[N-(1-adamantyl)-N-methylamino]butyrate, 3-[N-(1-adamantyl-N-methylamino)]propionic acid and their pharmaceutically acceptable salts. These compounds are particularly useful in the treatment of parkinsonism.

5 Claims, No Drawings

COMPOSITIONS USEFUL FOR TREATING PARKINSONISM

This is a division of application Ser. No. 408,021, filed 10-19-73.

This invention relates to compounds of the formula:

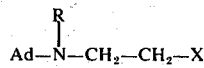

wherein Ad is 1-adamantyl; R is H or $CH_3$; X is COOM or $CH_2$

wherein M is H or a pharmaceutically acceptable cation, and $R_1$ is lower n-alkyl; and the pharmaceutically acceptable salts thereof.

More specifically this invention relates to [N-(1-adamantyl)-N-methylamino]lower alkanoic acid derivatives, such as 3-[N-(1-adamantyl)-N-methylamino]propionic acid, the lower n-alkyl esters of 4-[N-(1-adamantyl)-N-methylamino]butyric acid, their pharmaceutically acceptable salts and intermediates in their preparation, and to processes for using said compositions. 3-[N-(1-adamantylamino)]propionic acid is an intermediate in the preparation of 3-[N-(1-adamantyl)-N-methylamino]propionic acid while the lower n-alkyl ester of 4-[N-(1-adamantylamino)]butyric acid is an intermediate in the preparation of the lower n-alkyl ester of 4-[N-(1-adamantyl)-N-methylamino]butyric acid.

The invention, in its process of using aspect, comprises treating symptoms of parkinsonism by administering to a mammal exhibiting parkinsonism a therapeutically effective quantity of at least one of the above N-(1-adamantyl)-N-methylamino acids.

A still more specific and preferred representation of the composition of matter aspect of this invention are the chemical compositions ethyl-4-[N-(1-adamantyl)-N-methylamino]butyrate and 3-[N-(1-adamantyl)-N-methylamino]propionic acid, their pharmaceutically acceptable salts and pharmaceutical compositions thereof. Ethyl-4-[N-(1-adamantylamino)]butyrate is an intermediate in the preparation of ethyl-4-[N-(1-adamantyl)-N-methylamino]butyrate.

The compounds of the present invention may be prepared by the following reaction schemes wherein Ad = 1-adamantyl, Et = ethyl, and R = a lower n-alkyl:

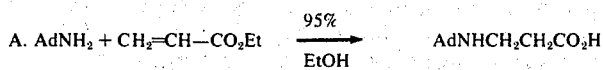

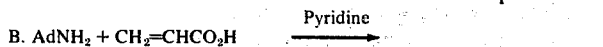

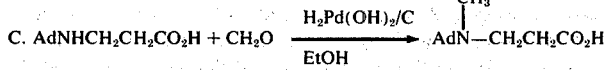

In reaction scheme A, aminoadamantane is reacted with ethyl acrylate in 95% ethanol to yield 3-[N-(1-adamantylamino)]propionic acid (I). The latter can alternatively be prepared by reacting aminoadamantane with acrylic acid in pyridine as shown in reaction scheme B. The 3-[N-(1-adamantylamino)]propionic acid (I) is hydrogenated with formalin, a 37% aqueous formaldehyde solution, and ethanol in the presence of palladium hydroxide on carbon (Pearlman catalyst) to yield 3-[N-(1-adamantyl)-N-methylamino]propionic acid (II).

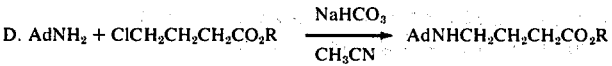

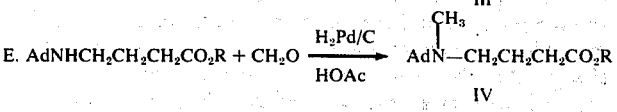

In reaction scheme D, aminoadamantane is reacted with a lower alkyl 4-chlorobutyrate and sodium bicarbonate in acetonitrile to yield the lower alkyl ester 4-[N-(1-adamantylamino)]butyric acid (III). This in turn is hydrogenated in reaction scheme E with formalin, a 37% aqueous formaldehyde solution, and acetic acid in the presence of palladium on charcoal to yield lower n-alkyl-4-[N-(1-adamantyl)-N-methylamino]butyrate (IV).

The "lower alkyl" radicals as used herein are linear, contain 1-6 carbon atoms, and include methyl, ethyl, n-propyl, n-butyl, n-amyl, and n-hexyl. Preferred is ethyl.

Exemplary of the pharmaceutically acceptable acid addition salts of the butyrate are those formed with maleic, fumaric, succinic, tartaric, citric, malic, cinnamic, sulfonic, hydrochloric, hydrobromic, sulfuric, phosphoric, and nitric acids. These salts may be prepared in the conventional manner by treating a solution or suspension of the free base in an organic solvent with the desired acid, and then recovering the salt which forms by crystallization techniques.

The propionic acid may be salified with a "pharmaceutically acceptable cation." This includes any cation which forms salts of the 3-[N-(1-adamantylamino)]-propionic acid which do not create any difference in kind of pharmaceutical activity from that shown by the corresponding free acid. Such cations may be used to provide greater solubility or greater ease in formulation than the corresponding free acid. Representative of such salts are those wherein the cation is an alkali metal such as sodium or potassium, ammonium, substituted ammonium such as diethanolammonium or such metal cations as calcium or aluminum. The propionic acid may also be hydrated.

Parkinsonism is a degenerative disease of the nervous system. The disease is manifest by its three cardinal characteristics: involuntary tremors, rigidity, and akinesia. Extrapyramidal syndromes exhibited with this condition include gait and postural abnormalities, oculargyric crisis and profuse salivation.

Attempts at treating these symptoms have involved the use of such classes of drugs as for example, antihistamines (diphenhydramine), anticholinergics (atropine sulfate, trihexyphenidyl) and amphetamines (dextroamphetamine sulfate) with varying degrees of success. However, these drugs, due to their inherent side effects, have a somewhat limited degree of utility. For example, anticholinergics may precipitate acute glaucoma in certain individuals; antihistamines may cause drowsiness, and amphetamines and similar central nervous system (C.N.S.) stimulants are contraindicated in those patients also having cardiac conditions.

Recently the use of L-dopa and amantadine hydrochloride, a drug first used for its antiviral activity, has been introduced for treating symptoms of parkinsonism. These drugs, although promising, require high dosages and exhibit debilitating side effects which severely limit their utility. It is an object of this invention to provide a new agent with an improved therapeutic index for treating the manifestations of the disease.

In tests in rats, the compositions of this invention exhibit a greater therapeutic index (T.I.) than corresponding doses of amantadine hydrochloride required to achieve a comparable response. Concomitant with this greater therapeutic index, there is a marked decrease in the debilitating side effects which may accompany the administration of amantadine hydrochloride, e.g. nervousness, insomnia, psychic reactions and ataxia.

Based upon standard laboratory tests and procedures, the effective dosage of the active ingredient of the compositions of this invention is considered to be within the range of from about 0.3 to 6 mg. per kg. of mammalian body weight per day. For ethyl-4-[N-(1-adamantyl)-N-methylamino]butyrate the dosage range can be between about 50 to 400 mg. per 70 kg. per day. While for 3-[N-(1-adamantyl)-N-methylamino]propionic acid the dosage range can be between 25 to 200 mg. per 70 kg. per day. The daily dosage is preferably administered in divided doses. The exact dosage administered will of course be dependent upon the age, weight, and progression of the disease in the recipient.

The compounds of this invention may be administered alone or combined with other medicaments. In any event, a suitable pharmaceutically acceptable carrier is generally employed. A carrier is selected according to the route of administration to be used, i.e. orally or parenterally, as well as according to the physical properties of the compounds and standard pharmaceutical practice. The oral route is preferred. The carrier should not react chemically with the compound to be administered. The preparations containing the active ingredients of this invention may be in the form of tablets, capsules, syrups, elixirs, suspensions, suppositories and the like. In the formulations of pharmaceutical preparations there can be employed such pharmaceutically acceptable diluents as for example, water, gelatin, lactose, starches, magnesium stearate, talc, vegetable oils, gums and theobroma oil.

The invention will be described in greater detail with respect to the following illustrative, but non-limiting examples:

EXAMPLE 1

3-[N-(1-adamantylamino)]propionic acid

A. Method A

Reflux a mixture of 117.76 g. (0.78 moles) of 1-aminoadamantane, also called amantadine, and 78.0 g. (0.78 moles) of ethyl acrylate in 750 ml. of 95% ethanol for one week. Filter off the analytically pure product, m.p. 208°–209°C.

B. Method B

Reflux a mixture of 45.3 g. (0.3 moles) of 1-aminoadamantane and 21.6 g. (0.3 moles) of acrylic acid in 600 ml. of dry pyridine for 3 hours and then let the mixture stand at room temperature overnight. Remove the solvent in vacuo, stir the residue with 300 ml. of acetone and filter off the solids. Sublime the filter cake at 150°C (0.1 mm.) to give the analytically pure product.

EXAMPLE 2

Ethyl-4-[N-(1-adamantylamino)]butyrate

Reflux a mixture of 24.02 g. (0.16 moles) of ethyl 4-chlorobutyrate, 25.7 g. (0.17 moles) of 1-aminoadamantane and 40.0 g. (0.48 moles) of sodium bicarbonate in 250 ml. of acetonitrile with adequate stirring for about 1 week. Cool the mixture to room temperature; pour it into 1.4 liters of icewater; extract with ether; dry over anhydrous sodium sulfate; filter; evaporate the filtrate and distill the residue, collecting the fraction boiling at 113°–116°C (0.05 mm.). Dissolve this fraction, which is the free base, in ether and acidify with 5.24 M ethereal hydrogen chloride; filter off the resulting solid and crystallize it from methanol-ethyl acetate to give the analytically pure hydrochloride salt of the product of this example, m.p. 221.0°–222.0°C (decomp).

EXAMPLE 3

3-[N-(1-adamantyl)-N-methylamino]-propionic acid

Hydrogenate a mixture of 5.575 g. (0.0250 moles) of 3-[N-(1-adamantylamino)]-propionic acid, 4.05 g. (0.050 moles) of 37% aqueous formaldehyde (formalin) and 50 ml. of ethanol in the presence of 0.07 g. of 20% palladium hydroxide on carbon (Pearlman catalyst) at 53 psi for 17 days. Filter, concentrate the filtrate in vacuo at 50°C, azeotropically remove the residual solvent with benzene and triturate the residue with ether to give the analytically pure product of this example, m.p.=147.0°–149.0°C (dec.).

EXAMPLE 4

Ethyl 4-[N-(1-adamantyl)-N-methylamino]butyrate

Hydrogenate a mixture of 11.1 g. (0.042 moles) of ethyl 4-[N-(1-adamantyl)amino]butyrate, 6.8 g. (0.084 moles) of 37% formalin and 150 ml. of acetic acid in the presence of 0.5 g. of 5% palladium on carbon at 60 psi for 2 days. Filter, pour the filtrate into 500 ml. of icewater, basify with 65 g. of 50% sodium hydroxide followed by 25 ml. of 10% sodium carbonate, saturate with sodium chloride, extract into ether, dry over anhydrous sodium sulfate, filter and acidify the filtrate, which is the free base (b.p. 135°–136°C (0.1 mm)) with a solution of 8.5 ml. of 5.24 M ethereal hydrogen chloride. Filter off the resulting solid and crystallize it from ethyl acetate to give the analytically pure hydrochloride salt of the product of this example, m.p. 206.5°–207.5°C (decomp).

EXAMPLE 5:

Formulations

The following illustrate typical tablet and capsule formulations incorporating the compositions of this invention.

I. Tablet Formulations
Formula and Method of Manufacture for ethyl-4-[(1-adamantyl)-4-methyl-amino]butyrate

| Coated Tablets: | mg.-core |
|---|---|
| Ethyl-4-[N-(1-adamantyl)-N-methylamino] butyrate hydrochloride | 4 |
| Lactose, U.S.P. | 62 |
| Dicalcium Phosphate | 40 |
| Sodium Lauryl Sulfate | 10 |
| Polyvinylpyrrolidone | 10 |
| Water 50 ml./1000 cores | |
| Corn Starch | 20 |

| Dry | m.g.-core |
|---|---|
| Sodium Lauryl Sulfate | 2 |
| Magnesium Stearate | 2 |
| Tablet Weight | 150 |

Procedure:

Mix the ethyl-4-[N-(1-adamantyl)-N-methylamino]butyrate hydrochloride with the lactose, dicalcium phosphate, and sodium lauryl sulfate. Screen the above mixture through a No. 60 screen and granulate with an aqueous solution containing polyvinylpyrrolidone. Add additional water, if necessary to bring powders to a pasty mass. Add corn starch and continue mixing until uniform granules are formed. Pass through a No. 10 screen, tray and dry in oven at 100°C for 12 to 14 hours. Reduce the dried granulation through a No. 16 screen, add sodium lauryl sulfate and magnesium stearate, mix and compress into desired shape on a tablet machine.

Coating:

Treat the above cores with a lacquer and dust with talc to prevent moisture absorption. Add sub-coat layers to round out the core. Apply a sufficient number of lacquer coats to make the core enteric. Apply additional sub-coats and smoothing coats to completely round out and smooth the tablet. Apply color coats until desired shade is obtained. After drying, polish the coated tablets to give the tablets an even gloss.

II. Capsule Formulations

| Formula: | m.g./capsule |
|---|---|
| 3-[N-(1-adamantyl)-N-methylamino] propionic acid hydrate | 4 |
| Sodium Lauryl Sulfate | 20 |
| Lactose | 150 |
| Magnesium Stearate | 76 |
| | 250 |

Procedure:

Mix together 3-[N-(1-adamantyl)-N-methylamino]propionic acid, lauryl sulfate and lactose. Pass through a No. 80 screen. Add magnesium stearate, mix and encapsulate into the proper size two-piece gelatin capsule.

III. Suppository Formulations

| Formula: | m.g./2gm. |
|---|---|
| Ethyl-4-[N-(1-adamantyl)-N-methylamino] butyrate hydrochloride | 8 |
| Theobroma Oil, Pharm. Grade to make | 2 gms. |

Procedure:

Prepare a slurry of ethyl-4-[N-(1-adamantyl)-N-methyl-amino]butyrate hydrochloride with melted theobroma oil to bring the batch to final weight. Pour the melted mix, while maintaining uniformity, into appropriately prepared molds and allow to cool.

Variations of the above compositions of matter and processes for the manufacture will be apparent to one skilled in the art within the spirit of the present invention.

I claim:

1. A process for treating symptoms of parkinsonism, which comprised administering to a mammal suffering from parkinsonism a therapeutically effective quantity of an N-adamantylmethylamino derivative selected from the group consisting of 3-[N-(1-adamantylamino)]propionic acid and a lower n-alkyl ester of 4-[N-(1-adamantyl)-N-methylamino]butyric acid and a pharmaceutically acceptable salt thereof.

2. The process of claim 1 wherein 3-[N-(1-adamantylamino)]propionic acid is used.

3. The process of claim 1 wherein ethyl-4[N-(1-adamantyl)-N-methylamino]butyrate is used.

4. The process of claim 1 wherein ethyl-4[N-(1-adamantyl)-N-methylamino]butyrate hydrochloride is used.

5. A pharmaceutical composition for the treatment of the symptoms of parkinsonism which comprises an amount effective to alleviate the symptoms of parkinsonism of an N-adamantylamino compound selected from the group consisting of 3-[N-(1-adamantylmethylamino)]propionic acid and the lower alkyl ester of 4-[N-(1-adamantyl)-N-methylamino]butyric acid and the pharmaceutically acceptable salts thereof together with a pharmaceutically acceptable carrier compatible with said compound.

* * * * *